United States Patent
Lee et al.

(10) Patent No.: US 11,938,457 B2
(45) Date of Patent: Mar. 26, 2024

(54) APPARATUS FOR PREPARING OLIGOMER

(71) Applicant: LG CHEM, LTD., Seoul (KR)

(72) Inventors: Hong Min Lee, Daejeon (KR); Jeong Seok Lee, Daejeon (KR); Jong Hun Song, Daejeon (KR); Kyung Seog Youk, Daejeon (KR); Dong Kwon Lee, Daejeon (KR); Moon Sub Hwang, Daejeon (KR)

(73) Assignee: LG Chem, Ltd., Seoul (KR)

( * ) Notice: Subject to any disclaimer, the term of this patent is extended or adjusted under 35 U.S.C. 154(b) by 188 days.

(21) Appl. No.: 17/432,083

(22) PCT Filed: Nov. 13, 2020

(86) PCT No.: PCT/KR2020/015981
§ 371 (c)(1),
(2) Date: Aug. 18, 2021

(87) PCT Pub. No.: WO2021/145545
PCT Pub. Date: Jul. 22, 2021

(65) Prior Publication Data
US 2022/0143568 A1    May 12, 2022

(30) Foreign Application Priority Data
Jan. 14, 2020   (KR) .................. 10-2020-0004722

(51) Int. Cl.
*B01J 19/18*        (2006.01)
*B01J 4/00*         (2006.01)
(Continued)

(52) U.S. Cl.
CPC ............ *B01J 19/18* (2013.01); *B01J 4/002* (2013.01); *B01J 4/004* (2013.01); *B01J 19/006* (2013.01);
(Continued)

(58) Field of Classification Search
None
See application file for complete search history.

(56) References Cited

U.S. PATENT DOCUMENTS

| | | | |
|---|---|---|---|
| 2,689,267 A | 9/1954 | Rollman | |
| 4,168,918 A * | 9/1979 | de Jonge | B08B 9/093 366/330.1 |

(Continued)

FOREIGN PATENT DOCUMENTS

| | | |
|---|---|---|
| CN | 1558884 A | 12/2004 |
| CN | 103561859 A | 2/2014 |

(Continued)

*Primary Examiner* — Jennifer A Leung
(74) *Attorney, Agent, or Firm* — Bryan Cave Leighton Paisner LLP

(57) ABSTRACT

The present disclosure relates to an apparatus for preparing an oligomer, the apparatus including: a reactor for oligomerizing a feed stream containing a fed monomer; a stirrer inserted into a hole formed in an upper portion of the reactor; and a solvent transfer line extending inward from a side of the reactor, wherein the stirrer includes a rotating shaft vertically extending downward from the upper portion of the reactor, and a blade having a conical shape whose vertex is positioned at a lower end of the rotating shaft and outer diameter increases from a bottom toward a top, and the solvent transfer line has a plurality of spray nozzles formed in a direction toward the blade.

10 Claims, 2 Drawing Sheets

(51) Int. Cl.
  *B01J 19/00*  (2006.01)
  *C07C 2/08*  (2006.01)

(52) U.S. Cl.
  CPC ............ *B01J 19/0066* (2013.01); *C07C 2/08* (2013.01); *B01J 2219/00247* (2013.01); *B01J 2219/00779* (2013.01)

(56) References Cited

U.S. PATENT DOCUMENTS

| | | | |
|---|---|---|---|
| 2005/0020866 A1* | 1/2005 | Kobayashi | .............. C08F 10/00 585/502 |
| 2005/0051484 A1 | 3/2005 | Wolf et al. | |
| 2017/0190637 A1 | 7/2017 | Emoto | |

FOREIGN PATENT DOCUMENTS

| | | |
|---|---|---|
| CN | 204429762 U | 7/2015 |
| CN | 105032301 A | 11/2015 |
| CN | 207641085 U | 7/2018 |
| JP | H11060512 A | 3/1999 |
| JP | 2000-237567 A | 9/2000 |
| JP | 3382160 B2 | 3/2003 |
| JP | 2005-97602 A | 4/2005 |
| JP | 4165053 B2 | 10/2008 |
| JP | 2009-504808 A | 2/2009 |
| JP | 5166662 B2 | 3/2013 |
| KR | 20020004001 A | 1/2002 |
| KR | 10-2004-0099973 A | 12/2004 |
| KR | 20190110958 A | 10/2019 |
| WO | WO-2015193797 A1 * | 12/2015 ............ B01J 10/002 |

\* cited by examiner

APPARATUS FOR PREPARING OLIGOMER

CROSS-REFERENCE TO RELATED APPLICATIONS

This application is a National Phase entry pursuant to 35 U.S.C. § 371 of International Application No. PCT/KR2020/015981, filed on Nov. 13, 2020, and claims the benefit of and priority to Korean Patent Application No. 10-2020-0004722, filed on Jan. 14, 2020, the disclosures of which are incorporated by reference in their entirety for all purposes as if fully set forth herein.

TECHNICAL FIELD

The present invention relates to an apparatus for preparing an oligomer, and more particularly, to an apparatus for preparing an oligomer for improving the stabilization of an entire process by reducing the amount of entrained solids and liquids in a reactor during the production of the oligomer

BACKGROUND ART

Alpha-olefin, which is an important substance used for a comonomer, a detergent, a lubricant, a plasticizer, etc., has been commercially widely used, and among them, 1-hexene and 1-octene have been mainly used as a comonomer for adjusting density of polyethylene during the production of linear low density polyethylene (LLDPE).

The alpha-olefin such as 1-hexene and 1-octene has been typically produced through an oligomerization reaction of ethylene. The ethylene oligomerization reaction is performed by an oligomerization reaction (trimerization reaction or tetramerization reaction) of ethylene using ethylene as a reactant in the presence of a catalyst, and the product produced through the above reaction produces not only a multi-component hydrocarbon mixture containing the desired 1-hexene and 1-octene, but also a small amount of by-products containing C20+ polymer materials during catalytic reaction. These by-products are accumulated not only in an inner wall of the reactor, but also in post-processing apparatuses such as a condenser, a pipe, and a valve, thereby causing fouling. As such, the fouling that occurs in the post-processing apparatuses of the reactor causes poor performance and mechanical damage in the apparatus, and in the worst case, the operation of an entire process should be shut down, resulting in a decrease in production due to a decrease in operating time and an increase in a cost incurred during a cleaning process.

Thus, in order to solve the problems described above, a study is needed to reduce the amount of entrained solids and liquids containing a polymer in the reactor.

DISCLOSURE

Technical Problem

The present invention has been made in an effort to solve the problems described above, and an object of the present invention is to provide an apparatus for preparing an oligomer for improving the stabilization of an entire process by preventing entrainment of by-products containing C20+ polymer materials other than a desired product in the reactor.

Technical Solution

In one aspect, there is provided an apparatus for preparing an oligomer, the apparatus including: a reactor for oligomerizing a feed stream containing a monomer; a stirrer inserted into a hole formed in an upper portion of the reactor; and a solvent transfer line extending inward from a side of the reactor, wherein the stirrer includes a rotating shaft vertically extending downward from the upper portion of the reactor, and a blade having a conical shape whose vertex is positioned at a lower end of the rotating shaft and outer diameter increases from a bottom toward a top, and the solvent transfer line has a plurality of spray nozzles formed in a direction toward the blade.

Advantageous Effects

According to an apparatus for preparing an oligomer of the prevent invention, stabilization of an entire process can be improved by installing a stirrer having a conical blade formed in a reactor to reduce the amount of entrained non-vapors such as solids and liquids in the reactor.

In addition, the apparatus for preparing an oligomer according to the present invention includes a solvent transfer line having a plurality of spray nozzles formed toward the conical blade and capable of spraying a solvent, which can remove contaminants accumulated on an outer surface of the blade.

In addition, the apparatus for preparing an oligomer according to the present invention can effectively increase the cycle of shutting down the operation of the reactor by preventing fouling from occurring in the post-processing apparatuses of the reactor, and can save an energy cost by preventing an efficiency degradation due to fouling of the post-processing apparatuses.

DETAILED DESCRIPTION

The terms and words used in the detailed description and claims of the present invention should not be interpreted as being limited to conventional or dictionary meanings, but should be interpreted as having meanings and concepts meeting the technical ideas of the present invention based on a principle that the inventors can appropriately define the concepts of terms in order to describe their own inventions in the best mode.

In the present invention, the term "stream" may refer to a flow of fluid in a process, and may also refer to fluid itself flowing in a moving line (pipe). Specifically, the "stream" may refer to both of fluid itself flowing in a pipe connecting respective apparatuses to each other and a flow of the fluid. In addition, the fluid may mean that any one or more of gas, liquid, and solid is included.

In the present invention, the term "C#" in which "#" is a positive integer refers to all hydrocarbons having # carbon atoms. Thus, the term "C10" refers to a hydrocarbon compound having 10 carbon atoms. In addition, the term "C#+" refers to all hydrocarbon molecules having # or more carbon atoms. Thus, the term "C10+" refers to a mixture of hydrocarbons having 10 or more carbon atoms.

Figure 1:
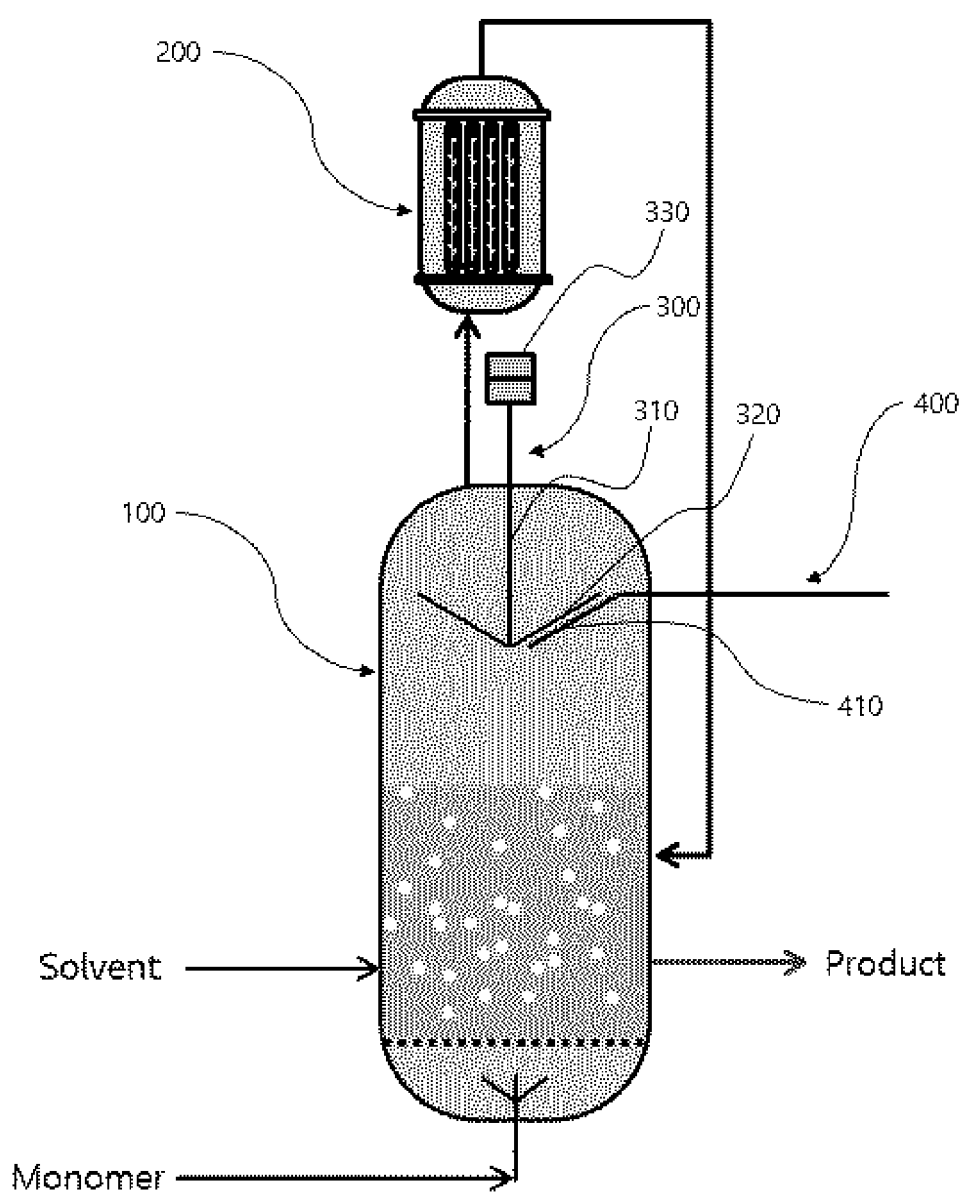
FIG. 1 is a process flow chart illustrating an apparatus for preparing an oligomer according to an exemplary embodiment of the present invention.
Figure 2:
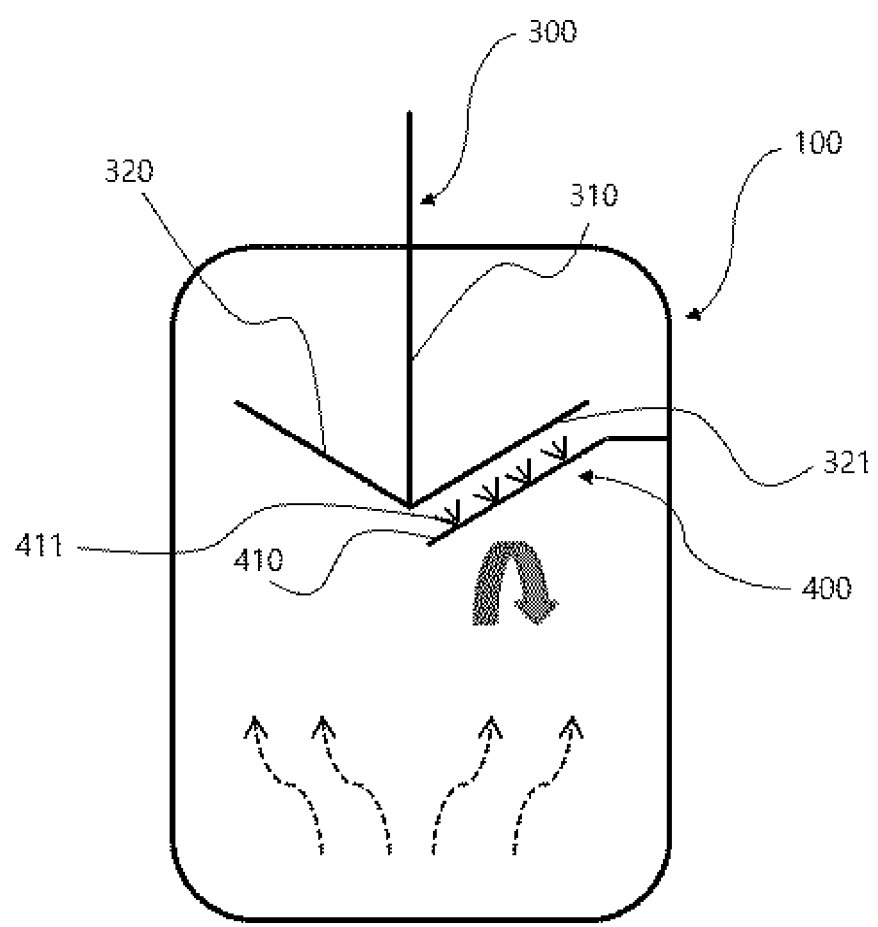
FIG. 2 is an enlarged view illustrating a part of the apparatus for preparing an oligomer according to an exemplary embodiment of the present invention.

Hereinafter, in order to help understand the present invention, the present invention will be described in more detail with reference to FIGS. 1 and 2 below.

According to the present invention, there is provided an apparatus for preparing an oligomer. The apparatus for preparing an oligomer includes: a reactor 100 for oligomerizing a feed stream containing a monomer; a stirrer 300 inserted into a hole formed in an upper portion of the reactor 100; and a solvent transfer line 400 extending inward from a side of the reactor 100, wherein the stirrer 300 includes a rotating shaft 310 vertically extending downward from the upper portion of the reactor 100, and a blade 320 having a conical shape whose vertex is positioned at a lower end of the rotating shaft 310 and outer diameter increases from a bottom toward a top, and the solvent transfer line 400 has a plurality of spray nozzles 411 formed in a direction toward the blade 320.

According to an exemplary embodiment of the present invention, the reactor 100 can produce an oligomer product by performing an oligomerization reaction of a monomer in the presence of a catalyst and a solvent.

According to an exemplary embodiment of the present invention, the reactor 100 can be a reactor 100 suitable for a continuous process. For example, the reactor 100 can include one ore more reactors selected from the group consisting of a continuous stirred-tank reactor, a plug flow reactor, and a bubble column reactor. This allows the oligomer product to be produced continuously.

According to an exemplary embodiment of the present invention, the monomer can include ethylene. Specifically, a feed stream containing an ethylene monomer can be fed to the reactor 100 and subjected to the oligomerization reaction to produce a desired alpha olefin product. In this case, the oligomerization reaction can be performed in a lower to middle region of the reactor 100, and the oligomerization reaction of the monomer can be performed in a liquid reaction medium dissolved in a solvent in the presence of a catalyst and a cocatalyst. As such, the region made of the reaction medium in which the oligomerization reaction of a monomer is performed can be defined as a reaction region. The oligomerization reaction can refer to a reaction in which a monomer is oligomerized. Depending on the number of monomers to be polymerized, the oligomerization reaction is called trimerization and tetramerization, which are collectively called multimerization.

The alpha-olefin, which is an important substance used for a comonomer, a detergent, a lubricant, a plasticizer, etc., is commercially widely used, and among them, 1-hexene and 1-octene are mainly used as a comonomer for controlling a density of polyethylene during the production of linear low density polyethylene (LLDPE). The alpha-olefin such as 1-hexene and 1-octene can be produced, for example, through a trimerization reaction or a tetramerization reaction of the ethylene.

According to an exemplary embodiment of the present invention, the oligomerization reaction of the monomer can be performed as a homogeneous liquid-phase reaction using the reaction system and conventional contact techniques under the presence or absence of a solvent, a slurry reaction in which the catalyst is partially insoluble or entirely insoluble, a two-phase liquid/liquid reaction, or a bulk-phase or gas-phase reaction in which a product acts as a main medium.

The solvent can be fed into the position lower than the reaction region inside the reactor 100 through a lower side of the reactor 100. The solvent can include, for example, one or more selected from the group consisting of n-pentane, n-hexane, n-heptane, cyclohexane, methylcyclohexane, octane, cyclooctane, decane, dodecane, benzene, xylene, 1,3,5-trimethylbenzene, toluene, ethylbenzene, chlorobenzene, dichlorobenzene, and trichlorobenzene.

The catalyst can include a transition metal source. The transition metal source can be, for example, a compound including one ore more selected from the group consisting of chromium(III) acetylacetonate, chromium(III) chloride tetrahydrofuran, chromium(III) 2-ethylhexanoate, chromium (III) tris (2,2,6,6-tetramethyl-3,5-heptanedionate), chromium(III) benzoylacetonate, chromium(III) hexafluoro-2,4-pentanedionate, chromium(III) acetate hydroxide, chromium(III) acetate, chromium(III) butyrate, chromium (III) pentanoate, chromium(III) laurate, and chromium(III) stearate.

The cocatalyst can include, for example, one or more selected from the group consisting of trimethyl aluminium, triethyl aluminium, triisopropyl aluminium, triisobutyl aluminum, ethylaluminum sesquichloride, diethylaluminum chloride, ethyl aluminium dichloride, methylaluminoxane, modified methylaluminoxane, and borate.

According to an exemplary embodiment of the present invention, the feed stream containing the monomer can be fed into the reactor 100 through the lower portion of the reactor 100. In this case, the feed stream can be fed into the reactor 100 in a gaseous state.

The gaseous feed stream fed into the reactor 100 passes through the liquid reaction medium in which a solvent and a catalyst exist, while the oligomerization reaction proceeds through the catalytic reaction, and in this case, gas and liquid are mixed as a reaction medium to exist in two phases. The oligomer product produced through the oligomerization reaction of the monomer can be discharged as a liquid second discharge stream, and an unreacted monomer not subjected to the oligomerization reaction in the reaction medium can be discharged as a gaseous first discharge stream.

Specifically, the first discharge stream of the reactor 100 can contain an unreacted monomer that did not participate in the oligomerization reaction of the monomer and a solvent. As such, the first discharge stream containing the unreacted monomer and the solvent can be fed into a condenser 200. The first discharge stream condensed in a liquid phase in the condenser 200 is refluxed to the reaction region of the reactor and can be reused for the oligomerization reaction.

In addition, the second discharge stream of the reactor 100 can include the oligomer product produced through the oligomerization reaction of the monomer, and a solvent. In this case, the oligomer product and the solvent can be separated through an additional separation apparatus (not illustrated), and the separated solvent can be reused in a process for preparing an oligomer. In addition, for example, when the oligomerization reaction is performed using an ethylene monomer as the monomer, the oligomer product can include 1-hexene and 1-octene.

In the reactor 100, a solid polymer is produced as by-products, in addition to a desired oligomer product, due to the catalytic reaction of the monomer, and is suspended in the liquid reaction medium. In this case, the solid polymer and a liquid solvent are entrained with a gaseous unreacted monomer at a speed at which the feed stream containing a large amount of gaseous monomers is introduced, and are discharged as the first discharge stream of the reactor 100. In this case, fouling occurs in the condenser 200, a pipe (not illustrated), and a valve (not illustrated), which are post-treatment apparatuses of the reactor 100, due to the adhesion of the polymer.

On the other hand, the present invention can improve the stability of the entire process by installing a stirrer 300 having a conical blade 320 formed in the reactor 100 to prevent entrainment of by-products including polymer in addition to the desired oligomer product to prevent fouling in the post-processing apparatus.

In addition, the apparatus for preparing an oligomer according to the present invention includes a solvent transfer line 400 having a plurality of spray nozzles 411 formed toward the conical blade 320 and capable of spraying a solvent, which can remove contaminants accumulated on an outer surface of the blade 320 in real time.

Further, the apparatus for preparing an oligomer according to the present invention can effectively increase the cycle of shutting down the operation of the reactor 100 by preventing fouling from occurring in the post-processing apparatus of the reactor 100, and can save an energy cost by preventing an efficiency degradation due to fouling of the post-processing apparatus.

According to an exemplary embodiment of the present invention, the apparatus for preparing an oligomer can include a stirrer 300 inserted into a hole formed in an upper portion of the reactor 100. For example, the hole formed in the upper portion of the reactor 100 can be formed in the center of the reactor 100. In addition, the stirrer 300 can be inserted into and fixed in a hole formed in the upper portion of the reactor 100.

The stirrer 300 can include a rotating shaft 310 vertically extending downward from the upper portion of the reactor, and a blade 320 having a conical shape whose vertex is positioned at a lower end of the rotating shaft 310 and outer diameter increases from the bottom toward the top.

The rotating shaft 310 is a central shaft when the stirrer 300 rotates, and the stirrer 300 can rotate about the rotating shaft 310. In addition, the rotational motion of the rotating shaft 310 can cause the blade 320 formed at the lower end of the rotating shaft 310 to rotate.

The rotating shaft 310 extends vertically downward from the upper portion of the reactor 100, and a length of the rotating shaft 310 can freely extend in a region between interfaces of the reaction medium in the upper portion of the reactor 100.

The blade 320 is fixed to the lower end of the rotating shaft 310, has a conical shape whose vertex is positioned at the lower end of the rotating shaft 310 and outer diameter increases from the bottom toward the top, and can be formed entirely in a V-shape when viewed in the longitudinal section.

The blade 320 rotates according to the rotational motion of the rotating shaft 310, the rotating shaft 310 is connected to a driving portion 330 such as a motor, and the driving portion 330 performs a function of rotating the rotating shaft 310.

When the blade 320 rotates, a part of a gaseous stream moving from the lower portion to the upper portion of the reactor 100 can be guided in a downward direction of the reactor 100 due to the rotation of the blade 320.

The gaseous stream can refer to, for example, a gaseous first discharge stream discharged from the reactor 100, and the gaseous first discharge stream contains non-vapor in a solid state such as a polymer and non-vapor in a liquid state such as a liquid drop in the process of moving to the upper portion of the reactor 100.

As such, the non-vapor entrained in the reactor 100 can be guided in the downward direction of the reactor 100 due to airflow formed by rotating the blades 320, and thus, the amount of the polymer entrained in the gaseous first discharge stream discharged to the upper portion of the reactor 100 can be significantly reduced.

In addition, the occurrence of fouling can be prevented in the condenser 200 for condensing the first discharge stream, which is installed in the upper portion of the reactor 100, by reducing the amount of the polymer entrained in the first discharge stream, and thus heat exchange efficiency of the condenser 200 can be increased to save energy.

In addition, the gaseous stream guided in the downward direction of the reactor 100 contains an unreacted monomer due to the rotation of the blade 320, and can increase a conversion rate into the oligomer by being circulated into a reaction medium and reused for the oligomerization reaction.

The blade 320 can have a vertex angle of 45° to 150°, 60° to 130°, or 90° to 130°. The blade 320 can have a vertex angle within the above range to effectively remove non-vapor entrained in the first discharge stream. Specifically, the larger the vertex angle of the blade 320, the wider the range to prevent entrainment, and at the same time, the higher the possibility of fouling. Thus, it is important to properly adjust the vertex angle of the blade 320.

The outer surface of the blade 320 can include an inclined portion 321 inclined at a predetermined angle from a vertex toward a top about the rotating shaft. Contaminants such as the polymer entrained in the rising first discharge stream can be attached to and accumulated on the inclined portion 321. As such, when the contaminants are accumulated on the inclined portion 321 of the blade 320, it can be immediately removed due to the plurality of spray nozzles 411 formed in the solvent transfer line 400 to be described later.

According to an exemplary embodiment of the present invention, the solvent transfer line 400 extending inward from the side of the reactor 100 can be included. Specifically, the solvent transfer line 400 can be formed to extend from the side surface of the reactor 100 to a region spaced apart from the inner wall of the reaction 100.

The solvent transfer line 400 can be installed to prevent the attachment and accumulation of the contaminants such as polymers on the blade 320.

A plurality of spray nozzles 411 can be formed in the solvent transfer line 400 in a direction toward the blade 320. Specifically, the solvent transfer line 400 can include a spray portion 410 in which the spray nozzle is formed, and a plurality of spray nozzles 411 can be formed in the spray portion 410.

The plurality of spray nozzles 411 can be installed in a direction toward the blade 320 to spray a solvent toward the blade 320. Specifically, the solvent sprayed through the plurality of spray nozzles 411 can be sprayed toward the inclined portion 321 of the outer surface of the blade 320.

The solvent transfer line 400 can be fixed to the reactor 100. Specifically, the solvent transfer line 400 can be inserted into and fixed in a hole formed on the side of the reactor 100. In this case, the shape of the solvent transfer line 400 is not particularly limited, and the material can be formed as a pipe used in the art as long as it is a material that is not corroded by a solvent.

The spray portion 410 of the solvent transfer line 400 can have a slope corresponding to the inclined portion 321 of the outer surface of the blade 320, and can be disposed to be spaced apart from the inclined portion by a predetermined interval. Specifically, in the solvent transfer line 400, the spray portion 410 in which the plurality of spray nozzles 411 are formed can be disposed to be spaced apart from the inclined portion 321 by a predetermined interval so as to have a slope, shape, and length corresponding to the inclined portion 321 of the outer surface of the blade 320.

As such, the spray portion 410 of the solvent transfer line 400 has a slope corresponding to the inclined portion 321 of the outer surface of the blade 320 and is disposed to be spaced apart from the inclined portion 321 by a predetermined interval, such that a solvent can be sprayed on the inclined portion 321 of the blade 320 through a plurality of spray nozzles 411 formed on the spray portion 410.

The spray portion 410 of the solvent transfer line 400 is fixed to the reactor 100, the inclined portion 321 of the outer surface of the blade 320 is rotated due to the rotational motion of the rotation shaft 310 of the stirrer 300, and the spray portion 410 and the inclined portion 321 can be disposed to be spaced apart from each other by a predetermined interval in order to minimize friction in this process.

In addition, the solvent can be sprayed toward the outer surface of the blade 320 through a plurality of spray nozzles 411 formed in the solvent transfer line 400 fixed to the reactor 100, and in this case, as the stirrer 300 rotates, the blade 320 rotates, and the contaminants accumulated on the outer surface of the blade 320 can be dissolved in a solvent sprayed through the spray nozzle 411 and removed therefrom.

The solvent sprayed through the plurality of spray nozzles 411 can be the same as the solvent used for the oligomerization reaction of the feed stream containing monomers in the reactor 100. The solvent can include, for example, one or more selected from the group consisting of n-pentane, n-hexane, n-heptane, cyclohexane, methylcyclohexane, octane, cyclooctane, decane, dodecane, benzene, xylene, 1,3,5-trimethylbenzene, toluene, ethylbenzene, chlorobenzene, dichlorobenzene, and trichlorobenzene. As such, the same solvent as the solvent used in the oligomerization reaction is used, such that the dissolving power for the polymer is excellent, and the inflow of external factors into the reactor 100 can be prevented, thereby improving stability.

The temperature of the solvent sprayed through the plurality of spray nozzles 411 can be 100 to 300° C. For example, the temperature of the solvent can be 130° C. to 250° C., 150° C. to 250° C., or 150° C. to 200° C. When a high-temperature solvent within the above range is sprayed onto the inclined portion 321 of the outer surface of the blade 320, the contaminants accumulated on the inclined portion 321 can be effectively removed.

2 to 10, 3 to 8, or 3 to 6 spray nozzles 411 can be formed on the spray portion 410. The number of the spray nozzles can be easily changed depending on the diameter of the reactor 100 and the size of the blade 320 of the stirrer 300 changed accordingly.

The plurality of spray nozzles 411 can include at least one spray port. In addition, the spray nozzle 411 can be implemented in the form of a spray including a plurality of spray ports. For example, the spray nozzle 411 can have 1 to 5, 1 to 4, or 2 to 4 spray ports. Referring to FIG. 1 as an example, the spray nozzle 411 can be implemented with three spray ports.

In the spray portion 410, a plurality of spray nozzles 411 can be arranged in a line at predetermined intervals.

In the spray portion 410, the pressure of the solvent sprayed through the plurality of spray nozzles 411 can be 1 bar·g to 100 bar·g. For example, the spray pressure of the solvent can be 3 bar·g to 80 bar·g, 5 bar·g to 75 bar·g, or 20 bar·g to 70 bar·g. The contaminants accumulated on the inclined portion 321 of the outer surface of the blade 320 can be effectively removed by spraying the solvent at a pressure within the above range.

In the spray portion 410 in which the plurality of spray nozzles 411 of the solvent transfer line 400 are formed, each of the spray nozzles 411 can have different pressures for spraying the solvent. For example, the contaminants accumulated on the inclined portion 321 of the outer surface of the blade 320 can be removed more efficiently by varying the spray pressure of the plurality of spray nozzles 411 arranged to be spaced apart from the spray portion 410 in a line at predetermined intervals.

In the plurality of spray nozzles 411 formed on the solvent transfer line 400, the closer to the inner wall of the reactor 100, the higher the spray pressure of the solvent can be.

Specifically, the mixed vapor (vapor+non-vapor) rises in a non-uniform state by the vortex in the region adjacent to the inner wall of the reactor 100, and the mixed vapor rises between the blade 320 and the inner wall of the reactor 100, and thus, in the outer surface of the blade 320, a large amount of contaminants can be accumulated on a region adjacent to the inner wall of the reactor 100, that is, a region far from the vertex of the blade 320.

Accordingly, in the plurality of spray nozzles 411, the closer to the inner wall of the reactor 100, that is, the further away from the vertex of the blade 320, the higher the spray pressure of the solvent is adjusted, such that the contaminants accumulated on the outer surface of the blade 320 can be efficiently removed.

According to an embodiment of the present invention, the apparatus for preparing the oligomer can further install apparatuses required to produce the oligomer, such as a valve, a condenser, a reboiler, a pump, a cooling facility, a filter, a stirrer, a separation apparatus, a compressor and a mixer, if necessary.

The apparatus for preparing an oligomer according to the present invention has been described and has been shown in the drawings herein, but only essential configurations for understanding the present invention have been described and have been illustrated in the drawings, and processes and apparatuses that are not separately described and illustrated, in addition to processes and apparatus described above and illustrated in the drawings, may be appropriately applied and used in order to implement the apparatus for preparing an oligomer according to the present invention.

The invention claimed is:

1. An apparatus for preparing an oligomer, the apparatus comprising:
   a reactor for oligomerizing a feed stream containing a monomer;
   a stirrer inserted into a hole formed in an upper portion of the reactor; and
   a solvent transfer line extending inward from a side of the reactor;
   wherein the stirrer includes a rotating shaft vertically extending downward from the upper portion of the reactor, and a blade having a conical shape whose vertex is positioned at a lower end of the rotating shaft and an outer diameter of the blade increases from a bottom toward a top,
   wherein the solvent transfer line has a plurality of spray nozzles formed in a direction toward the blade,
   wherein an outer surface of the blade includes an inclined portion inclined at a predetermined angle from the vertex to the top about the rotating shaft,
   wherein the solvent transfer line includes a spray portion in which the plurality of spray nozzles are formed, and wherein the spray portion has a slope corresponding to the inclined portion and is disposed to be spaced apart from the inclined portion by a predetermined interval.

2. The apparatus of claim 1, wherein a part of a gaseous stream moving from a lower portion to the upper portion of the reactor is guided in a downward direction of the reactor due to the blade.

3. The apparatus of claim 1, wherein the plurality of spray nozzles formed in the spray portion of the solvent transfer line spray a solvent toward the inclined portion.

4. The apparatus of claim 3, wherein the spray nozzles are configured to spray the solvent having a temperature of 100° C. to 300° C.

5. The apparatus of claim 3, wherein the spray nozzles are configured to spray the solvent having a pressure of 1 bar·g to 100 bar·g.

6. The apparatus of claim 1, wherein each of the plurality of spray nozzles has a different pressure for spraying the solvent with each other.

7. The apparatus of claim 6, wherein in the plurality of spray nozzles formed in the solvent transfer line, the closer to an inner wall of the reactor, the higher the spray pressure of the solvent.

8. The apparatus of claim 1, wherein the blade has a vertex angle of 45° to 150°.

9. The apparatus of claim 1, wherein the solvent transfer line is fixed to the reactor.

10. The apparatus of claim 1, wherein the plurality of spray nozzles formed in the solvent transfer line are configured to spray a solvent toward an outer surface of the blade to remove contaminants accumulated on the outer surface of the blade when the stirrer rotates.

* * * * *